(12) United States Patent
Fujiwara et al.

(10) Patent No.: US 8,383,532 B2
(45) Date of Patent: *Feb. 26, 2013

(54) GLASS FLAKE

(75) Inventors: Kosuke Fujiwara, Tokyo (JP); Akihiro Koyama, Tokyo (JP); Koichi Sakaguchi, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 112 days.

This patent is subject to a terminal disclaimer.

(21) Appl. No.: 12/305,850

(22) PCT Filed: Jun. 21, 2007

(86) PCT No.: PCT/JP2007/062510
§ 371 (c)(1),
(2), (4) Date: Dec. 19, 2008

(87) PCT Pub. No.: WO2007/148758
PCT Pub. Date: Dec. 27, 2007

(65) Prior Publication Data
US 2010/0183737 A1 Jul. 22, 2010

(30) Foreign Application Priority Data
Jun. 23, 2006 (JP) .................. 2006-174060

(51) Int. Cl.
*C03C 3/087* (2006.01)
*C09C 1/28* (2006.01)
*C09D 11/00* (2006.01)
*C08K 3/22* (2006.01)
*C08K 3/34* (2006.01)
*A61K 33/08* (2006.01)

(52) U.S. Cl. .......... 501/70; 424/613; 424/691; 428/402; 428/404; 428/432; 106/403; 106/489; 106/31.13; 524/413; 524/433

(58) Field of Classification Search ................... 501/70, 501/33; 428/403, 406
See application file for complete search history.

(56) References Cited

U.S. PATENT DOCUMENTS

| | | | |
|---|---|---|---|
| 4,882,302 A | 11/1989 | Horiuchi et al. | |
| 5,789,329 A | 8/1998 | Eastes et al. | |
| 6,136,735 A * | 10/2000 | Gallo et al. | 501/36 |
| 6,686,304 B1 * | 2/2004 | Wallenberger | 501/35 |
| 7,189,671 B1 * | 3/2007 | Lewis | 501/36 |
| 7,700,682 B2 * | 4/2010 | Sekine | 524/494 |
| 2002/0193233 A1 | 12/2002 | Kishimoto et al. | |
| 2003/0019501 A1 | 1/2003 | Hirota et al. | |
| 2003/0207748 A1 | 11/2003 | Wallenberger | |
| 2003/0224922 A1 * | 12/2003 | Wallenberger | 501/35 |
| 2004/0170838 A1 * | 9/2004 | Ambrosius et al. | 428/406 |

(Continued)

FOREIGN PATENT DOCUMENTS

| | | |
|---|---|---|
| CN | 1243501 | 2/2000 |
| CN | 1395481 A | 2/2003 |

(Continued)

*Primary Examiner* — Alicia Chevalier
*Assistant Examiner* — Ronak Patel
(74) *Attorney, Agent, or Firm* — Hamre, Schumann, Mueller & Larson, P.C.

(57) ABSTRACT

The glass flake of the present invention has a composition that includes, in terms of mass %, $60 < SiO_2 \leq 65$, $8 \leq Al_2O_3 \leq 15$, $47 \leq (SiO_2 - Al_2O_3) \leq 57$, $1 \leq MgO \leq 5$, $18 \leq CaO \leq 30$, $0 < Li_2O \leq 4$, $0 < (Li_2O + Na_2O + K_2O) \leq 4$, and $0 \leq TiO_2 \leq 5$, and that is substantially free from $B_2O_3$, F, ZnO, BaO, SrO, and $ZrO_2$.

27 Claims, 4 Drawing Sheets

U.S. PATENT DOCUMENTS

| | | | |
|---|---|---|---|
| 2005/0008850 A1 * | 1/2005 | Flynn et al. | 428/331 |
| 2005/0049133 A1 | 3/2005 | Fujiwara et al. | |
| 2006/0241205 A1 * | 10/2006 | Jia | 523/115 |
| 2008/0124559 A1 | 5/2008 | Fujiwara et al. | |

FOREIGN PATENT DOCUMENTS

| | | |
|---|---|---|
| EP | 0 165 530 A1 | 12/1985 |
| JP | 61-014152 A | 1/1986 |
| JP | 63-201041 A | 8/1988 |
| JP | 5-306143 | 11/1993 |
| JP | 9-143750 | 6/1997 |
| JP | 2001-213639 A | 8/2001 |
| JP | 2001-515448 A | 9/2001 |
| JP | 2004-508265 A | 3/2002 |
| JP | 2002-348141 | 12/2002 |
| JP | 5-000826 A | 1/2003 |
| JP | 2003-012962 A | 1/2003 |
| JP | 2003-500330 A | 1/2003 |
| JP | 2003-119690 A | 4/2003 |
| JP | 2003-137590 | 5/2003 |
| JP | 2003-246710 | 9/2003 |
| JP | 2004-011036 | 1/2004 |
| JP | 2005-506267 A | 3/2005 |
| JP | 2005-097080 A | 4/2005 |
| WO | 96/39362 | 12/1996 |
| WO | 00/73231 | 12/2000 |
| WO | WO 02/20419 A1 | 3/2002 |
| WO | WO 03/033425 A1 | 4/2003 |
| WO | WO 2006/068255 * | 6/2006 |
| WO | WO 2006-068255 A1 | 6/2006 |

\* cited by examiner

GLASS FLAKE

TECHNICAL FIELD

The present invention relates to glass flakes that can be mixed in, for example, resin moldings, coating materials, inks, and cosmetics. Furthermore, the present invention also relates to resin compositions, coating materials, ink compositions, and cosmetics containing the glass flakes.

BACKGROUND ART

Glass flakes allow resin moldings to have improved strength and dimensional accuracy when being dispersed, for example, in a resin matrix. These glass flakes are mixed in coating materials as liners and are then applied to metal or concrete surfaces.

Glass flakes exhibit metallic colors when the surfaces thereof are coated with metal. On the other hand, they exhibit interference colors due to interference of reflected light when the surfaces thereof are coated with metal oxides. That is, a glass flake coated with a coating film formed of metal or metal oxide also can be used as a luster pigment.

Luster pigments produced with glass flakes as described above are commonly used for applications such as coating materials and cosmetics where color tone and luster are considered to be important.

JP 63(1988)-201041 A describes, as suitable compositions for glass flakes, compositions of C glass produced with chemical durability being considered to be important, E glass developed for electronic products, and sheet glass.

JP 2001-213639 A describes glass flakes with excellent chemical durability. The glass flakes with excellent chemical durability contain neither diboron trioxide ($B_2O_3$) nor fluorine (F), which are volatile components, and the content of alkali metal oxides therein is 5 mass % or lower.

Glass compositions that are not flaky but fibrous with lower contents of alkali metal oxides are disclosed in the following publications:
JP 61(1986)-14152 A: "Glass Fiber"
JP 2001-515448 A: "Boron-Free Glass Fibers"
JP 2003-500330 A: "Glass Fiber Composition"
JP 2004-508265 A: "Glass Fiber Forming Compositions"
JP 2005-506267 A: "Glass Fiber Forming Compositions"

Glass flakes can be produced by using an apparatus described, for example, in JP 5(1993)-826 A. With the apparatus described in the publication, a molten glass base material is blown up into a balloon shape with a blow nozzle to form a hollow glass film, and this hollow glass film is crushed with a pressure roll. Thus glass flakes can be obtained.

When the production processes as described above are taken into consideration, glass flakes are required to have excellent meltability, a suitable temperature-viscosity property, and a lower devitrification temperature than a working temperature. In this case, the working temperature is a temperature at which glass has a viscosity of 1000 dPa·sec (1000 poise). Furthermore, the devitrification temperature is the temperature at which crystals are formed in the molten glass base material and start to grow. As to the temperature-viscosity property, the working temperature is preferably 1300° C. or lower because an excessively high working temperature particularly makes it difficult to form glass flakes. With the decrease in working temperature of the glass, the fuel cost required for melting glass raw materials can be reduced. Moreover, the decreased working temperature reduces the thermal damage to melting furnaces and apparatuses for producing glass flakes, allowing the life cycles of the furnaces and production apparatuses to be extended.

Apparatuses for producing glass flakes using centrifugal force, for example, have structural bodies, such as a cup that rotates at high speed to allow molten glass to flow out. Excessively high temperature of the molten glass deforms components of the structural bodies, leading to possible failure of the production apparatuses. Moreover, the production apparatuses tend to be eroded by the glass, resulting in shorter life cycles of the production apparatuses.

Furthermore, when a coating film made of metal or metal oxide is to be formed on the surface of a glass flake, the glass flake may be treated at a high temperature. Moreover, glass flakes or those with a coating film may be mixed in a coating material, which may be used for a baking finish to be treated at a high temperature, for example. Therefore glass flakes also are required to have a sufficiently high heat resistance.

Soda-lime glass that is used commonly as a so-called sheet glass composition contains a large amount of alkali metal oxides and therefore does not have a sufficiently high heat resistance, which has been a problem.

In the C glass composition and E glass composition among the compositions of the glass flakes described in JP 63(1988)-201041 A, diboron trioxide ($B_2O_3$) and fluorine (F) are essential components to be contained to adjust the devitrification temperature and viscosity. However, since diboron trioxide ($B_2O_3$) and fluorine (F) tend to volatilize, there is a possibility that they disperse during melting. Moreover, there also is a possibility of causing a problem in that, for example, they may erode the wall of a melting furnace or a regenerative furnace to reduce the furnace life.

Furthermore, in all the examples described in JP 2001-213639 A, glasses always contain any one component selected from zinc oxide (ZnO), barium oxide (BaO), strontium oxide (SrO), and zirconium oxide ($ZrO_2$).

However, since the zinc oxide (ZnO) tends to volatilize, there is a possibility that it disperses during melting. Furthermore, there is also a problem in that since it volatilizes, the content thereof in the glass is difficult to control.

Generally, the raw materials of barium oxide (BaO) are expensive. Some of them require to be handled with care.

The raw materials of strontium oxide (SrO) are expensive. They may contain raw materials of barium oxide (BaO). Therefore some of them require to be handled with care.

The zirconium oxide ($ZrO_2$) increases the devitrification growth rate of glass and thereby often makes it difficult to produce glass flakes stably.

From such reasons as described above, it is desirable not to use diboron trioxide ($B_2O_3$), fluorine (F), zinc oxide (ZnO), barium oxide (BaO), strontium oxide (SrO), and zirconium oxide ($ZrO_2$) in glass flakes.

Moreover, when consideration is given to the fact that the glass flakes are to be mixed in coating materials and cosmetics, they are required to have a high chemical durability.

DISCLOSURE OF INVENTION

With these situations in mind, the present invention is intended to provide glass flakes with a glass composition that is substantially free from diboron trioxide ($B_2O_3$), fluorine (F), zinc oxide (ZnO), barium oxide (BaO), strontium oxide (SrO), and zirconium oxide ($ZrO_2$) and that has excellent heat resistance, chemical durability, and formability.

The present inventors devoted themselves to make a series of studies about a glass composition that is suitable for glass flakes and that is substantially free from diboron trioxide ($B_2O_3$), fluorine (F), zinc oxide (ZnO), barium oxide (BaO), strontium oxide (SrO), and zirconium oxide (ZrO$_2$). As a result, they have found that when the composition ranges of SiO$_2$ and Al$_2$O$_3$, the composition range of (SiO$_2$—Al$_2$O$_3$) representing the relationship therebetween, and further, the composition ranges of alkali metal oxides are controlled, the chemical durability (especially acid resistance) is improved considerably and a glass composition that allows glass flakes to be formed easily can be obtained.

That is, the present invention provides a glass flake having a composition that includes, in terms of mass %:

60<SiO$_2$≦65,

8≦Al$_2$O$_3$≦15,

47≦(SiO$_2$—Al$_2$O$_3$)≦57,

1≦MgO≦5,

18≦CaO≦30,

0<Li$_2$O≦4

0<(Li$_2$O+Na$_2$O+K$_2$O)≦4, and

0≦TiO$_2$≦5, and that is substantially free from B$_2$O$_3$, F, ZnO, BaO, SrO, and ZrO$_2$.

According to the glass flake of the present invention, since it has excellent heat resistance, it is prevented from being deformed when being heated to a high temperature. The glass flake of the present invention is excellent in chemical durability, such as acid resistance, water resistance, and alkali resistance. Particularly, it has excellent acid resistance and therefore can be used as a corrosion-resistant liner in an acid environment. Furthermore, it also is useful as a substrate on which a coating film is to be formed by a liquid phase method using an acid solution. For example, a strong acid solution is used to form a titanium oxide coating film. In the above-mentioned composition ranges, since the working temperature can be controlled easily at a relatively low temperature, it is easy to form glass flakes.

Moreover, the present invention provides a glass flake with a coating film that includes the aforementioned glass flake and a coating film. The coating film is composed mainly of metal and/or metal oxide and covers a surface of the glass flake. The glass flake with a coating film can be used as a luster pigment. The term "mainly" denotes that the content of the component is the highest in terms of mass %.

These glass flakes or glass flakes with a coating film can be used in resin compositions, coating materials, ink compositions, and cosmetics by being added thereto.

BEST MODE FOR CARRYING OUT THE INVENTION

Figure 3A:
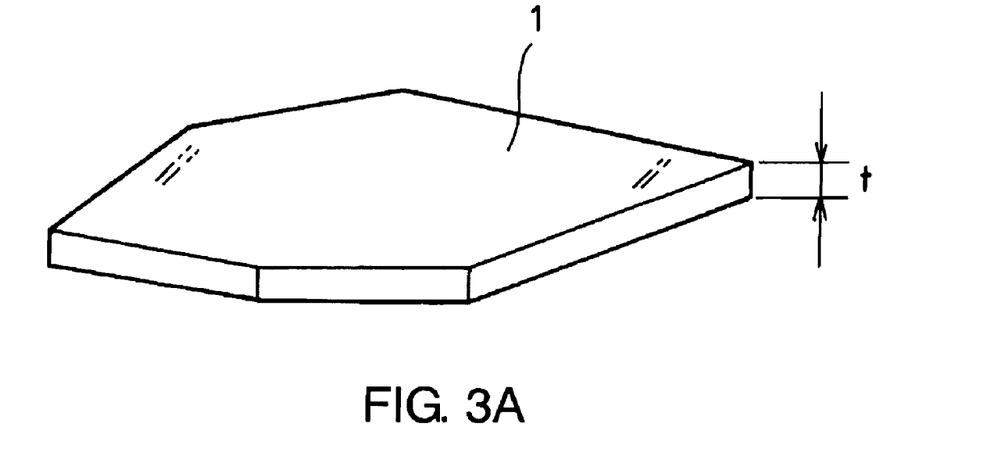
FIG. 3A is a schematic view of a glass flake according to the present invention.
Figure 3B:
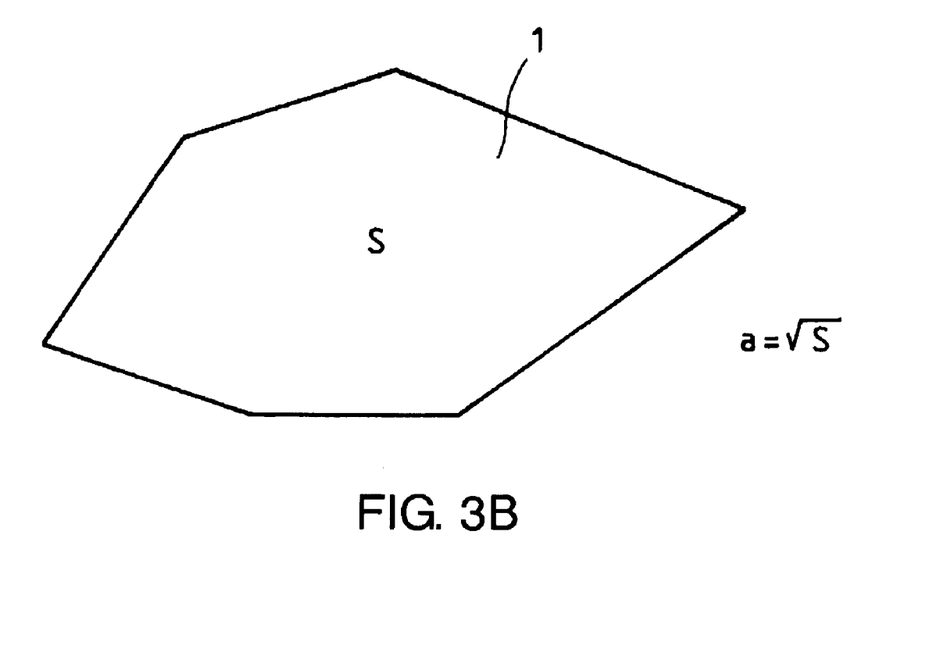
FIG. 3B is a plan view of a glass flake for describing a method of determining an average particle size.

As shown in FIG. 3A, a glass flake 1 may be a flaky particle with an average thickness t of 0.1 μm to 15 μm and an aspect ratio (average particle size a/average thickness t) of 2 to 1000. As shown in FIG. 3B, the average particle size a may be defined as the square root of the area S of the glass flake 1 viewed in plane.

Hereinafter, embodiments of the present invention will be described.

[Composition of Glass Flake]

The composition of the glass flakes of the present invention is described below in detail.

<SiO$_2$>

Silicon dioxide (SiO$_2$) is a main component forming the skeleton of glass. It also adjusts the viscosity and devitrification temperature during glass formation and also improves the acid resistance. When the SiO$_2$ content is 60 mass % or lower, the devitrification temperature becomes excessively high and therefore it becomes difficult to form glass flakes. Furthermore, the acid resistance of glass also is deteriorated. On the other hand, when the SiO$_2$ content exceeds 65 mass %, the melting point of glass becomes excessively high and therefore it becomes difficult to melt the raw materials uniformly. Accordingly, the lower limit of the SiO$_2$ content is preferably higher than 60 mass %. The upper limit of the SiO$_2$ content is preferably 65 mass % or lower, more preferably 63 mass % or lower, and further preferably 62 mass % or lower.

<Al$_2$O$_3$>

Aluminum oxide (Al$_2$O$_3$) is a component forming the skeleton of glass. It also adjusts the viscosity and devitrification temperature during glass formation and also improves the water resistance. On the other hand, it also deteriorates the acid resistance of glass. When the Al$_2$O$_3$ content is lower than 8 mass %, the viscosity and devitrification temperature cannot be adjusted sufficiently or the water resistance cannot be improved sufficiently. On the other hand, when the Al$_2$O$_3$ content exceeds 15 mass %, the melting point of glass becomes excessively high and therefore it becomes difficult to melt the raw materials uniformly, and the acid resistance also is deteriorated. Accordingly, the lower limit of the Al$_2$O$_3$ content is preferably at least 8 mass %, and more preferably at least 10 mass %. The upper limit of the Al$_2$O$_3$ content is preferably 15 mass % or lower, and more preferably lower than 12 mass %. The range of the Al$_2$O$_3$ content is selected from arbitrary combinations of these upper and lower limits.

<SiO$_2$—Al$_2$O$_3$>

The difference (SiO$_2$—Al$_2$O$_3$) between a component for improving the acid resistance of glass, SiO$_2$, and a component for deteriorating it, Al$_2$O$_3$, is important for the acid resistance of glass. When the difference (SiO$_2$—Al$_2$O$_3$) is lower than 47 mass %, the glass cannot have sufficiently high acid resistance. On the other hand, when the difference (SiO$_2$—Al$_2$O$_3$) exceeds 57 mass %, the devitrification temperature becomes excessively high and thereby it becomes difficult to form glass flakes. Accordingly, the lower limit of the difference (SiO$_2$—Al$_2$O$_3$) is preferably at least 47 mass %, and more preferably higher than 49 mass %. The upper limit of the difference (SiO$_2$—Al$_2$O$_3$) is preferably 57 mass % or lower, more preferably 55 mass % or lower, further preferably 54 mass % or lower, and most preferably 52 mass % or lower. The range of the difference (SiO$_2$—Al$_2$O$_3$) is selected from arbitrary combinations of these upper and lower limits.

<MgO and CaO>

Magnesium oxide (MgO) and calcium oxide (CaO) adjust the viscosity and devitrification temperature during glass formation.

When the MgO content is lower than 1 mass %, the viscosity and devitrification temperature cannot be adjusted sufficiently. On the other hand, when it exceeds 5 mass %, the devitrification temperature becomes excessively high and therefore it becomes difficult to form glass flakes. Accordingly, the lower limit of the MgO content is preferably at least 1 mass %, and more preferably at least 2 mass %. The upper limit of the MgO content is preferably 5 mass % or lower, and more preferably 4 mass % or lower. The range of the MgO content is selected from arbitrary combinations of these upper and lower limits.

When the CaO content is lower than 18 mass %, the viscosity and devitrification temperature cannot be adjusted sufficiently. On the other hand, when it exceeds 30 mass %, the devitrification temperature becomes excessively high and therefore it becomes difficult to form glass flakes. Accordingly, the lower limit of the CaO content is preferably at least 18 mass %, and more preferably at least 20 mass %. The upper limit of the CaO content is preferably 30 mass % or lower, and more preferably 25 mass % or lower, and further preferably 24 mass % or lower. The range of the CaO content is selected from arbitrary combinations of these upper and lower limits.

<$Li_2O$, $Na_2O$, and $K_2O$>

Alkali metal oxides ($Li_2O$, $Na_2O$, and $K_2O$) adjust the viscosity and devitrification temperature during glass formation. When no alkali metal oxide is contained, the melting point of glass becomes excessively high and therefore it becomes difficult to melt the raw materials uniformly, and it also becomes difficult to form glass flakes. On the other hand, when the sum of the contents of the alkali metal oxides ($Li_2O+Na_2O+K_2O$) exceeds 4 mass %, the glass transition temperature is low and the heat resistance of the glass is deteriorated. Accordingly, the lower limit of the sum ($Li_2O+Na_2O+K_2O$) is preferably higher than 0 mass %, and more preferably at least 0.4 mass %. The upper limit of the sum ($Li_2O+Na_2O+K_2O$) is preferably 4 mass % or lower, more preferably 3 mass % or lower, and further preferably lower than 2 mass %. The range of the sum ($Li_2O+Na_2O+K_2O$) is selected from arbitrary combinations of these upper and lower limits. When uniform melting of the raw material and the ease of forming of the glass flakes particularly are considered important, $2<(Li_2O+Na_2O+K_2O)\leq 4$ may hold.

Particularly, lithium oxide ($Li_2O$) is an essential component in the present invention. Lithium oxide ($Li_2O$) has an effect of lowering the melting point of glass. Accordingly, when it is contained, it becomes easy to melt glass raw materials uniformly. Furthermore, since $Li_2O$ is more effective than $Na_2O$ and $K_2O$ in lowering the working temperature, it becomes easy to form the glass flakes. On the other hand, when the $Li_2O$ content exceeds 4 mass %, the glass transition temperature is low and the heat resistance of the glass is deteriorated. Furthermore, the working temperature becomes excessively low with respect to the devitrification temperature, making it difficult to form the glass flakes. Accordingly, the lower limit of the $LiO_2$ content is preferably higher than 0 mass %, and more preferably at least 0.4 mass %. The upper limit of the $Li_2O$ content is preferably 4 mass % or lower, more preferably 3 mass % or lower, and further preferably lower than 2 mass %. The range of the $Li_2O$ content is selected from arbitrary combinations of these upper and lower limits. When uniform melting of the raw material and the ease of forming of the glass flakes particularly are considered important, $2<Li_2O\leq 4$ may hold.

<$TiO_2$>

Titanium oxide ($TiO_2$) improves the meltability and chemical durability as well as ultraviolet absorption properties of glass. Accordingly, when glass flakes containing $TiO_2$ are mixed, for example, in a resin matrix or coating material, they suitably can prevent the resin matrix or coating material from being deteriorated. However, when the $TiO_2$ content exceeds 5 mass %, the devitrification temperature of glass becomes excessively high and therefore it becomes difficult to form glass flakes. Accordingly, the lower limit of the $TiO_2$ content is preferably at least 0 mass %, and more preferably higher than 0 mass %. The upper limit of the $TiO_2$ content is preferably 5 mass % or lower, more preferably 3 mass % or lower, further preferably 2 mass % or lower, and most preferably lower than 2 mass %. The range of the $TiO_2$ content is selected from arbitrary combinations of these upper and lower limits.

<Fe>

Usually, iron (Fe) contained in glass is present in the state of $Fe^{2+}$ or $Fe^{3+}$. The components $Fe^{3+}$ and $Fe^{2+}$ improve the ultraviolet absorption properties and heat-ray absorption properties of glass, respectively. Accordingly, although iron (Fe) is not essential, it can be used as a component for adjusting the optical properties of glass. Moreover, iron (Fe) may be contained inevitably due to impurities in industrial raw materials even when it is not intended to be contained. When the iron (Fe) content is excessively high, coloring of glass becomes obvious. This coloring is sometimes not preferable to applications in which the color tone and luster of the glass flakes are considered to be important. Accordingly, the upper limit of the iron (Fe) content in terms of $Fe_2O_3$ is preferably 5 mass % or lower, more preferably 2 mass % or lower, still more preferably 0.5 mass % or lower, and further preferably 0.1 mass % or lower. Most preferably, no iron (Fe) is contained, substantially.

<$SO_3$>

Sulfur trioxide ($SO_3$) is not an essential component but can be used as a fining agent. When the raw materials of sulfate are used, 0.5 mass % or less of sulfur trioxide may be contained in some cases.

<$B_2O_3$>

Substantially no diboron trioxide ($B_2O_3$) is allowed to be contained in the present invention.

<F>

Substantially no fluorine (F) is allowed to be contained in the present invention.

<ZnO>

Substantially no zinc oxide (ZnO) is allowed to be contained in the present invention.

<BaO and SrO>

Substantially no strontium oxide (SrO) and barium oxide (BaO) are allowed to be contained in the present invention.

<$ZrO_2$>

Substantially no zirconium oxide ($ZrO_2$) is allowed to be contained in the present invention.

In the present invention, the expression "substantially no substance is allowed to be contained" denotes that it is not intended to be contained except for the case where it is contained inevitably, for instance, due to impurity in an industrial raw material. Specifically, that is the case where the substance content is lower than 0.1 mass %, preferably lower than 0.05 mass %, and more preferably lower than 0.03 mass %.

As described above, the glass composition of the glass flakes according to the present invention includes, as essential components, $SiO_2$, $Al_2O_3$, MgO, CaO and $Li_2O$, and preferably contains $TiO_2$. Furthermore, it can be composed of only these components. If necessary, it can contain $Na_2O$, $K_2O$, iron oxide (FeO and/or $Fe_2O_3$) or $SO_3$.

[Method for Manufacturing Glass Flakes]

Figure 1:
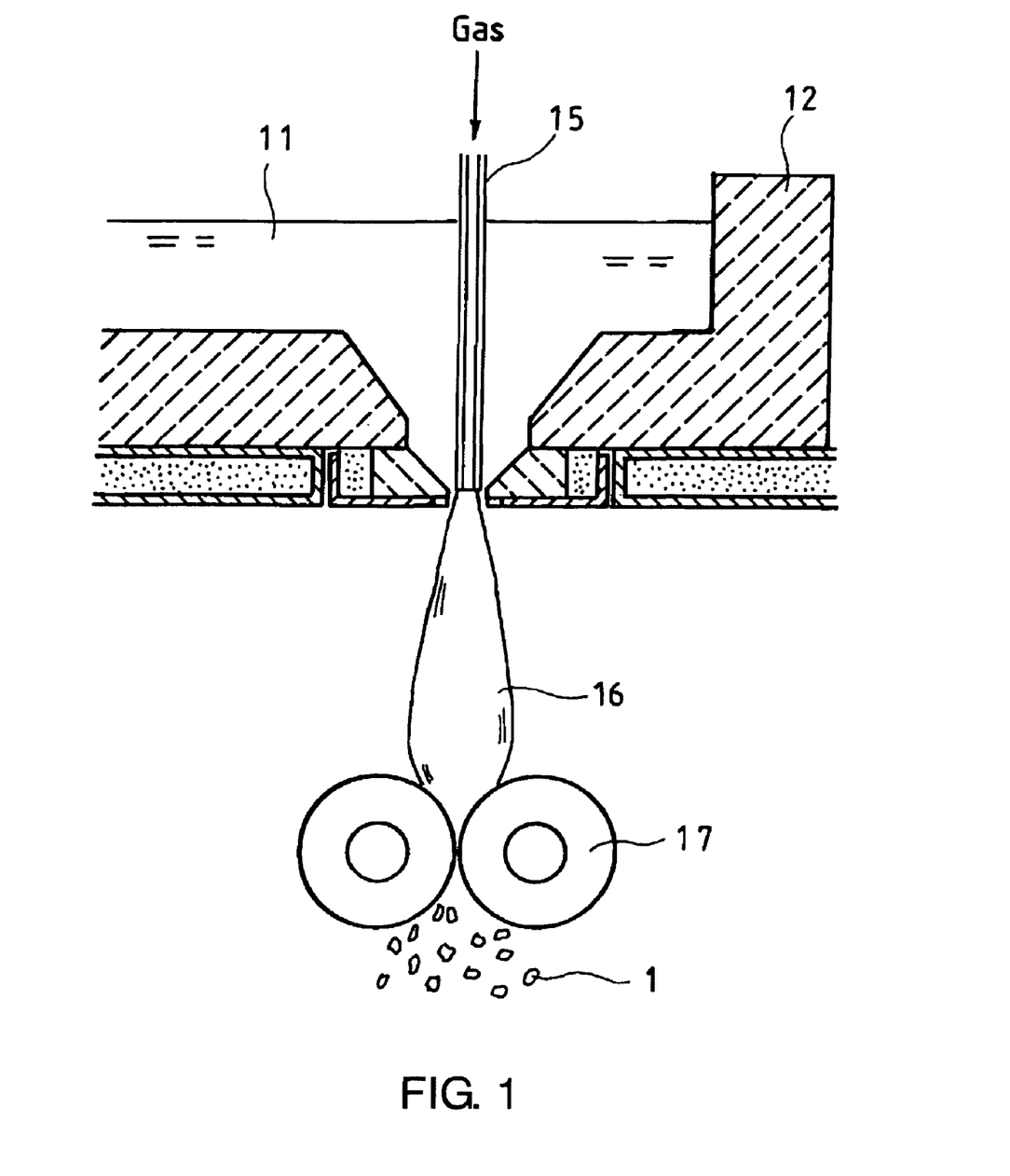
FIG. 1 is a schematic view for explaining an apparatus for producing glass flakes.

The glass flakes of the present invention can be produced, for example, using an apparatus as shown in FIG. 1. A glass base material 11 molten in a refractory furnace vessel 12 is blown up into a balloon shape with gas fed into a blow nozzle 15 to be formed into a hollow glass film 16. The hollow glass film 16 is crushed with pressure rolls 17 and thus glass flakes 1 are obtained.

Figure 2:
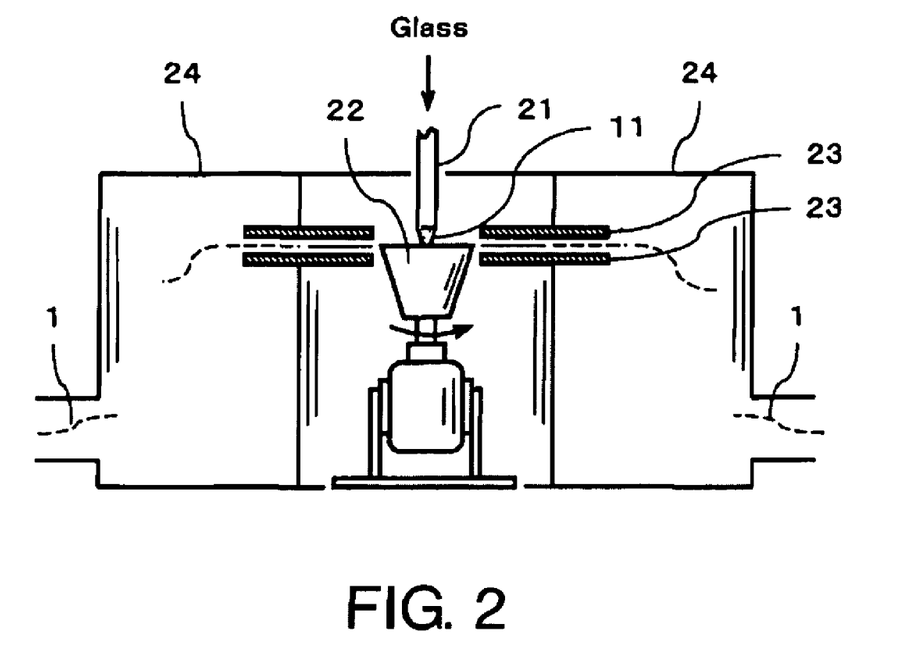
FIG. 2 is a schematic view for explaining an apparatus for producing glass flakes using centrifugal force.

The glass flakes of the present invention also can be produced, for example, using an apparatus as shown in FIG. 2. The molten glass base material 11 fed into a rotating cup 22 radially flows out of an upper end portion of the rotating cup 22 by centrifugal force, is then sucked by airflow through annular plates 23 and 23 disposed vertically, and is introduced into an annular cyclone-type collector 24. While traveling through the annular plates 23 and 23, the glass is cooled and solidified in the form of a thin film, and is further crushed into micro pieces. Thus, the glass flakes 1 are obtained.

[Physical Properties of Glass Flakes]

The respective physical properties of the glass flakes according to the present invention are described below in detail.

<Temperature Property>

The temperature at which the viscosity of molten glass is 1000 dPa·sec (1000 poise) is called "working temperature" and is considered to be the most suitable temperature for forming glass flakes.

According to the production apparatus of FIG. 1, for example, the hollow glass film 16 to make the glass flakes has an average thickness of 0.1 µm to 15 µm. When such a thin hollow glass film 16 is to be formed, the glass temperature decreases considerably. Accordingly, the plasticity of the hollow glass film 16 is deteriorated rapidly and it becomes difficult to be stretched. Furthermore, the deterioration in plasticity makes it difficult for the hollow glass film 16 to grow uniformly and thereby variations in glass film thickness may occur. Therefore, the working temperature is preferably at least 1100° C. and more preferably at least 1150° C.

However, when the working temperature exceeds 1300° C., the apparatus for producing glass tends to be corroded by heat and thus the apparatus life becomes shorter. With the decrease in working temperature, the fuel cost required for melting glass raw materials can be reduced. Therefore, the working temperature is preferably 1230° C. or lower, more preferably 1225° C. or lower, further preferably 1220° C. or lower, and most preferably 1215° C. or lower.

Furthermore, with an increase in temperature difference $\Delta T$ obtained by subtracting the devitrification temperature from the working temperature, devitrification tends not to occur during glass formation and thus more homogeneous glass flakes can be produced with a high yield. In the case of glass with a temperature difference $\Delta T$ of at least 0° C., glass flakes can be produced with a high yield, for example, using the production apparatus as shown in FIG. 1 or FIG. 2. Therefore, the temperature difference $\Delta T$ is preferably at least 0° C., more preferably at least 5° C., further preferably at least 10° C., and most preferably at least 15° C. However, the temperature difference $\Delta T$ is preferably lower than 50° C. because the glass composition can be adjusted easily in that case. Further preferably, the temperature difference $\Delta T$ is at most 40° C.

The term "devitrification" denotes that crystals that have been formed and have grown in a molten glass base material cause it to be cloudy. Glass produced from such a molten glass base material may contain crystallized mass and therefore is not preferred as glass flakes.

Furthermore, with an increase in temperature difference $\Delta K$ obtained by subtracting the softening point temperature from the working temperature, workability during glass flake formation is improved, and thus the thickness of the glass flakes tends to be adjusted easily. In the case of glass with a temperature difference $\Delta K$ of at least 342° C., the thickness of the glass flakes tends to be adjusted easily using, for example, the production apparatus as shown in FIG. 1 or FIG. 2. Therefore, the temperature difference $\Delta K$ is preferably at least 342° C., more preferably at least 345° C., further preferably at least 348° C., and most preferably at least 350° C.

<Glass Transition Point>

A higher glass transition point of glass flakes allows them to have higher heat resistance and to tend not to be deformed through processing that involves heating at a high temperature. When the glass transition point is at least 600° C., there is little possibility that the glass flakes will be deformed in the step of forming a coating film composed mainly of metal and/or metal oxide on the surface of each glass flake. Furthermore, glass flakes or glass flakes with a coating film can be mixed in a coating material, which can be used suitably for a baking finish, for example. The glass composition ranges defined in the present invention make it possible to obtain glass with a glass transition point of at least 600° C. easily. The glass transition point of the glass flakes is preferably at least 600° C., and more preferably at least 650° C.

<Chemical Durability>

The glass flakes of the present invention are excellent in chemical durability such as acid resistance, water resistance, and alkali resistance. Accordingly, the glass flakes of the present invention can be mixed suitably, for example, in resin moldings, coating materials, cosmetics, and inks.

The index of acid resistance to be used herein is a mass reduction rate $\Delta W_1$ obtained when granular glass with an average grain size of 420 µm to 590 µm was immersed in a 10-mass % sulfuric acid aqueous solution with a temperature of 80° C. for 72 hours. Lower mass reduction rates $\Delta W_1$ indicate higher acid resistance. The method of measurement thereof is in accordance with "Measuring Method for Chemical Durability of Optical Glass (Powder Method) 06-1975" of Japan Optical Glass Industrial Standards (JOGIS). However, a 10-mass % sulfuric acid aqueous solution is used in the examples described later instead of a 0.01N (mol/L) nitric acid aqueous solution used in the measurement method of JOGIS. Furthermore, the temperature of the sulfuric acid aqueous solution is set at 80° C., and the process time is 72 hours instead of 60 minutes employed in the measurement method of JOGIS.

When, for example, a coating material containing glass flakes is used as a corrosion-resistant liner in an acid environment, it is desirable that the glass have acid resistance of a small value in terms of the above-mentioned index (mass reduction rate $\Delta W_1$). When the weight reduction rate $\Delta W_1$ is high, the corrosion resistance to be provided by the corrosion-resistant liner in the acid environment is reduced. Accordingly, the weight reduction rate $\Delta W_1$ is preferably 0.8 mass % or lower, and further preferably 0.5 mass % or lower.

The alkali resistance can be measured by using a sodium hydroxide aqueous solution instead of the sulfuric acid aqueous solution employed for the method of measuring the acid resistance. The index of the alkali resistance to be used herein is a mass reduction rate $\Delta W_2$. The lower the mass reduction rate $\Delta W_2$, the higher the alkali resistance.

When glass flakes are used in a strong alkaline environment, for instance, in a battery separator, it is desirable that the alkali resistance of the glass in terms of the above-mentioned index (mass reduction rate $\Delta W_2$) be 3 mass % or lower.

When the weight reduction rate $\Delta W_2$ is higher than that, the components of the glass flakes elute into an electrolyte and the function of the separator may be damaged. The mass reduction rate $\Delta W_2$ is further preferably 2 mass % or lower.

[Glass Flakes with Coating Film]

Figure 4:
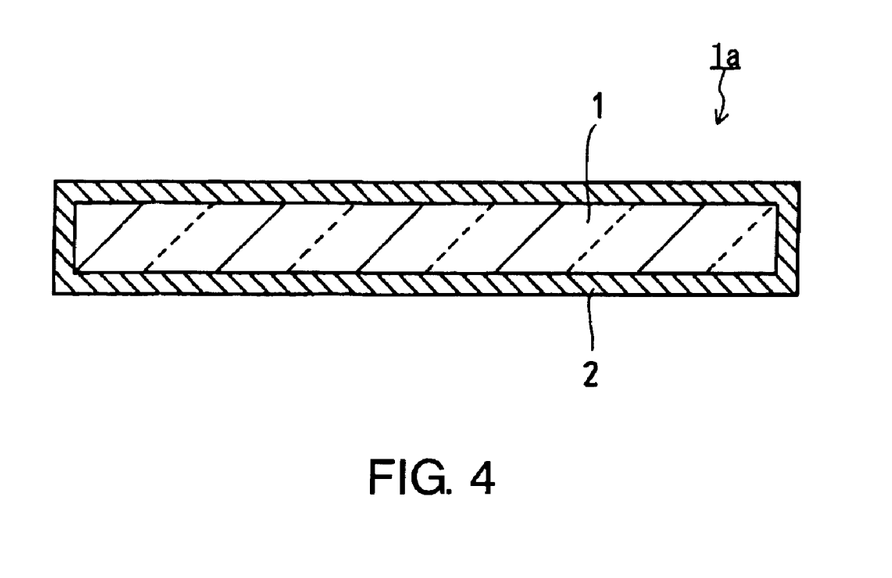
FIG. 4 is a schematic sectional view showing a glass flake with a coating film.

With the aforementioned glass flake 1 used as a substrate, a coating film 2 composed mainly of metal and/or metal oxide is formed on the surface thereof. Thus a glass flake with a coating film 1a can be produced (see FIG. 4). Preferably, the coating film 2 is formed substantially of metal and/or metal oxide. The coating film 2 can be in the form of a monolayer, a mixed layer, or multiple layers. The coating film 2 can be formed using at least one metal selected from the group consisting of silver, gold, platinum, palladium, and nickel.

Furthermore, the coating film 2 can be formed using at least one metal oxide selected from the group consisting of titanium oxide, aluminum oxide, iron oxide, cobalt oxide, zirconium oxide, zinc oxide, tin oxide, and silicon oxide. Especially, titanium dioxide and iron oxide are preferred. The titanium dioxide has a high refractive index and transparency and develops excellent interference colors. The iron oxide can develop characteristic interference colors.

Furthermore, the coating film 2 can be a layered film including a first film containing metal as its main component and a second film containing metal oxide as its main component. It is not necessary to form the coating film 2 on the whole surface of the glass flake 1 that serves as a substrate. The coating film 2 can be formed on part of the surface of the glass flake 1.

The thickness of the coating film 2 can be selected suitably according to the intended use. The method of forming the coating film 2 on the surface of the glass flake 1 can be any one of generally known methods. Examples of the method that can be used include known methods such as a sputtering method, a sol-gel method, a CVD method, an LPD method, and a liquid phase method in which oxides are allowed to deposit from metal salts onto the surface of the glass flake.

[Mixing of Glass Flakes in, For Example, Resin Compositions, Coating Materials, Ink Compositions, and Cosmetics]

The glass flake 1 or glass flake with a coating film 1a is mixed as a pigment or reinforcing filler, for example, in resin compositions, coating materials, ink compositions, or cosmetics by a known method. This improves the color tone and luster thereof as well as, for instance, dimensional accuracy and strength in the resin compositions, coating materials, and ink compositions.

Figure 5:
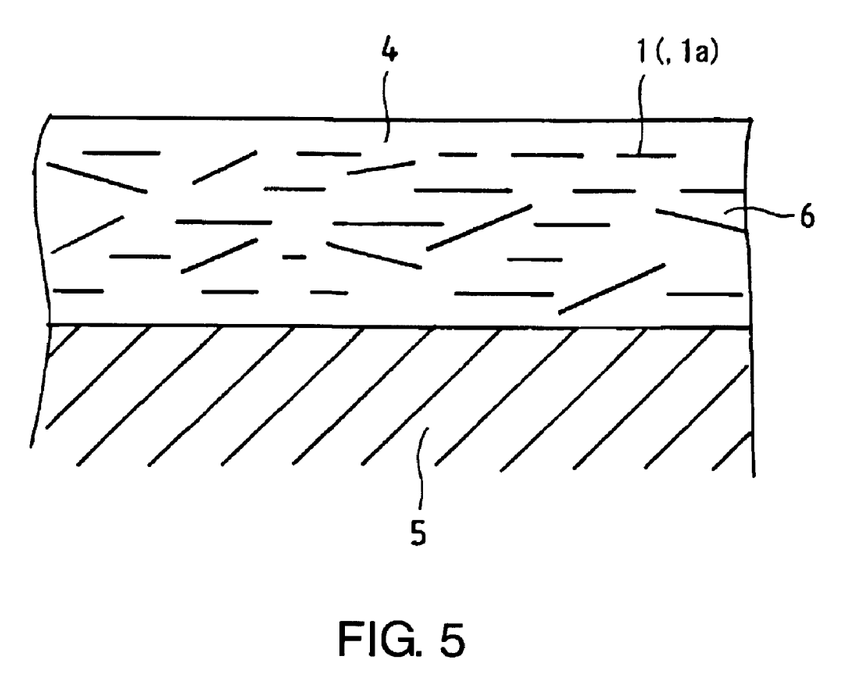
FIG. 5 is a schematic sectional view showing a resin composition containing glass flakes of the present invention.

FIG. 5 is a schematic sectional view for explaining an example in which the glass flakes 1 were mixed in a coating material, which then was applied to the surface of a substrate 5. The glass flakes 1 (or the glass flake with a coating film 1a) are dispersed in a resin matrix 4 of a coating film 6.

The resin composition, coating material, ink composition, and cosmetic to be used can be selected suitably according to the intended use as long as they are generally known. Furthermore, the mixing ratio between the glass flakes and the material to be mixed also can be selected suitably. Moreover, the method of mixing the glass flakes and the material together can be any method as long as it is generally known.

For instance, when the glass flakes are mixed in a coating material, a thermosetting resin, thermoplastic resin, or curing agent can be selected suitably to be used for a matrix resin.

Examples of the thermosetting resin include acrylic resin, polyester resin, epoxy resin, phenolic resin, urea resin, fluororesin, polyester-urethane curable resin, epoxy-polyester curable resin, acrylic-polyester resin, acrylic-urethane curable resin, acrylic-melamine curable resin, and polyester-melamine curable resin.

Examples of the thermoplastic resin include polyethylene resin, polypropylene resin, petroleum resin, thermoplastic polyester resin, and thermoplastic fluororesin.

Furthermore, examples of the curing agent include polyisocyanate, amine, polyamide, polybasic acid, acid anhydride, polysulfide, trifluoroborate, acid dihydrazide, and imidazole.

When the glass flakes are mixed in a resin composition, the aforementioned various thermosetting or thermoplastic resins can be used for the matrix resin.

Examples of the ink composition include inks for writing instruments, such as various kinds of ball-point pens and felt-tip pens, and printing inks, such as gravure ink and offset ink. Any one of them can be used as the ink composition.

The vehicle of the ink composition has a function of dispersing a pigment and fixing ink to paper. The vehicle is composed of, for example, resins, oil, and a solvent.

Vehicles of inks for writing instruments contain, as a resin, acrylic resin, styrene-acrylic copolymer, polyvinyl alcohol, polyacrylate, acrylic-vinyl acetate copolymer, microbially produced polysaccharide such as xanthan gum, or water-soluble plant polysaccharide such as guar gum. Furthermore, the vehicles contain, for example, water, alcohol, hydrocarbon, or ester as a solvent.

Vehicles for gravure inks contain, as a resin, gum rosin, wood rosin, toll oil rosin, lime rosin, rosin ester, maleic resin, polyamide resin, vinyl resin, cellulose nitrate, cellulose acetate, ethyl cellulose, chlorinated rubber, cyclized rubber, ethylene-vinyl acetate copolymer resin, urethane resin, polyester resin, alkyd resin, a resin mixture of, for example, gilsonite, dammar, or shellac, mixtures of the resins described above, aqueous emulsion resins or water-soluble resins obtained by water-solubilizing the resins described above. Furthermore, the vehicles contain, for example, hydrocarbon, alcohol, ether, ester, or water as a solvent.

Vehicles for offset inks contain: as a resin, rosin-modified phenolic resin, petroleum resin, alkyd resin, or a dry-modified resin thereof, and as oil, a plant oil such as linseed oil, tung oil, or soybean oil. Furthermore, the vehicles contain, for example, n-paraffin, isoparaffin, aromatic, naphthene, alpha-olefin, or water as a solvent.

Moreover, suitably selected common additives, such as dyes, pigments, various types of surfactants, lubricants, antifoaming agents, and leveling agents, can be mixed in the above-mentioned various vehicle components.

Examples of cosmetics include a wide range of cosmetics such as facial cosmetics, makeup cosmetics, and hair cosmetics. Among them, especially in makeup cosmetics such as foundation, face powder, eye shadow, blusher, makeup base, nail enamel, eyeliner, mascara, lipstick, and fancy powder, the glass flakes are used suitably.

The glass flakes can be subjected to a hydrophobizing treatment suitably accordingly to the purpose of the cosmetics. Examples of the method of carrying out the hydrophobizing treatment include the following five methods:

(1) a treatment method to be carried out using methyl hydrogen polysiloxane, high viscosity silicone oil, or a silicone compound such as a silicone resin;

(2) a treatment method to be carried out using a surfactant such as an anion activator or a cation activator;

(3) a treatment method to be carried out using a polymer compound such as nylon, polymethyl methacrylate, polyethylene, various types of fluororesins (such as polytetrafluoroethylene resin (PTFE), a tetrafluoroethylene-perfluoroalkyl vinyl ether copolymer (PFA), a tetrafluoroethylene-hexafluoropropylene copolymer (FEP), a tetrafluoroethylene-ethylene copolymer (ETFE), polyvinylidene fluoride (PVDF), and polychloro-trifluoroethylene (PCTFE)), or polyamino acid;

(4) a treatment method to be carried out using, for example, a perfluoro group-containing compound, lecithin, collagen, metallic soap, lipophilic wax, or polyhydric alcohol partial ester or whole ester; and (5) a treatment method employing a combination thereof.

However, any method other than the above-mentioned methods also can be used as long as it can be used generally for the hydrophobizing treatment of powder.

Moreover, other materials that are used usually for cosmetics can be mixed suitably in the cosmetics as required. Examples thereof include inorganic powder, organic powder, pigments, dyes, hydrocarbon, esters, oil components, organic solvents, resins, plasticizers, ultraviolet absorbers, antioxidants, preservatives, surfactants, moisturizing agents, fragrances, water, alcohol, and thickeners.

Examples of the inorganic powder include talc, kaolin, sericite, muscovite, phlogopite, lepidolite, biotite, lithia mica, vermiculite, magnesium carbonate, calcium carbonate, diatomaceous earth, magnesium silicate, calcium silicate, aluminum silicate, barium sulphate, metal tungstate, silica, hydroxyapatite, zeolite, boron nitride, and ceramic powder.

Examples of the organic powder include nylon powder, polyethylene powder, polystyrene powder, benzoguanamine powder, polytetrafluoroethylene powder, distyrenebenzene polymer powder, epoxy powder, acrylic powder, and microcrystalline cellulose.

Pigments are classified broadly into inorganic pigments and organic pigments. Examples of inorganic pigments, which are described by being broken down by color, include:
  inorganic white pigments: titanium oxide, zinc oxide, etc.;
  inorganic red pigments: iron oxide (red iron oxide), iron titanate, etc.;
  inorganic brown pigments: gamma iron oxide, etc.;
  inorganic yellow pigments: yellow iron oxide, yellow ocher, etc.;
  inorganic black pigments: black iron oxide, carbon black, etc.;
  inorganic violet pigments: mango violet, cobalt violet, etc.;
  inorganic green pigments: cobalt titanate, etc.; and
  inorganic blue pigments: ultramarine, indigo, etc.

Examples of pearl pigments include titanium oxide coated mica, titanium oxide coated bismuth oxychloride, bismuth oxychloride, titanium oxide coated talc, argentine, and colored titanium oxide coated mica. Furthermore, examples of metal powder pigments include aluminum powder and copper powder.

Examples of organic pigments include:
  red color No. 201, red color No. 202, red color No. 204, red color No. 205, red color No. 220, red color No. 226, red color No. 228, red color No. 405, orange color No. 203, orange color No. 204, yellow color No. 205, yellow color No. 401, and blue color No. 404; and
  organic pigments obtained by forming lakes of the following dyes with fillers such as talc, calcium carbonate, barium sulfate, zirconium oxide, or aluminum white:
  red color No. 3, red color No. 104, red color No. 106, red color No. 227, red color No. 230, red color No. 401, red color No. 505, orange color No. 205, yellow color No. 4, yellow color No. 5, yellow color No. 202, yellow color No. 203, green color No. 3, and blue color No. 1.

Furthermore, examples of dyes include natural dyes such as chlorophyll and beta-carotene.

Examples of hydrocarbon include:
  squalane, liquid paraffin, vaseline, microcrystalline wax, ozokerite, ceresin, myristic acid, palmitic acid, stearic acid, oleic acid, isostearic acid, cetyl alcohol, hexadecyl alcohol, oleyl alcohol, cetyl-2-ethyl hexanoate, 2-ethylhexyl palmitate, 2-octyldodecyl myristate, di-2-neopentylglycol ethyl hexanoate, tri-2-glycerol ethyl hexanoate, 2-octyldodecyl oleate, isopropyl myristate, glycerol triisostearate, glycerol tri-coconut oil fatty acid, olive oil, avocado oil, beeswax, myristyl myristate, mink oil, and lanoline;
  further silicone oil, higher fatty acid, esters of oils and fats, higher alcohol, and oil components such as wax; organic solvents such as acetone, toluene, butyl acetate, and ester acetate; resins such as alkyd resin and urea resin; plasticizers such as camphor and acetyl tributyl citrate; and ultraviolet absorbers, antioxidants, preservatives, surfactants, moisturizing agents, fragrances, water, alcohol, and thickeners.

The form of the cosmetics is not particularly limited. Examples thereof include powder, cake, pencil, stick, ointment, liquid, emulsion, and cream.

EXAMPLES

Hereinafter, the present invention is described further in detail using examples and comparative examples.

Examples 1 to 20 and Comparative Examples 1 to 16

Common glass raw materials such as silica were mixed together so that the compositions indicated in Tables 1 to 5 were obtained, and thereby batches of the respective examples and comparative examples were prepared. These batches were heated to 1400° C. to 1600° C. with an electric furnace to be melted. They were kept in this state for about four hours to have uniform compositions. Thereafter, each molten glass was poured onto an iron plate and was cooled slowly to normal temperature in the electric furnace. Thus glass samples were obtained.

Glasses thus produced were measured for thermal expansion coefficients using a commercial dilatometer and then glass transition points thereof were determined from the thermal expansion curves. Moreover, the relationship between viscosity and temperature was examined by a common platinum ball pulling method and then the working temperature was determined from the results. Further, crushed glass with a grain size of 1.0 mm to 2.8 mm was placed in a platinum boat and then was heated for two hours in an electric furnace with a temperature gradient (900° C. to 1400° C.). Then the devitrification temperature was determined from the maximum temperature of the place in the electric furnace corresponding to the position where a crystal appeared. The temperatures in the electric furnace have been measured beforehand according to positions and the glass placed in a predetermined position is heated at that temperature.

These measurement results are indicated in Tables 1 to 5. With respect to the glass compositions indicated in the tables, all the values are indicated in mass %. As described above, $\Delta T$ denotes the difference in temperature obtained by subtracting the devitrification temperature from the working temperature. As described above, $\Delta K$ denotes the difference in temperature obtained by subtracting the softening point temperature from the working temperature. As described above, $\Delta W_1$ denotes the index of acid resistance and is expressed by the mass reduction rate obtained when granular glass with an average grain size of 420 μm to 590 μm was immersed in a 10-mass % sulfuric acid aqueous solution with a temperature of 80° C. for 72 hours. As described above, $\Delta W_2$ denotes the index of the alkali resistance and is expressed by the mass reduction rate obtained when granular glass with an average grain size of 420 μm to 590 μm was immersed in a 10-mass % sodium hydroxide aqueous solution with a temperature of 80° C. for 72 hours.

TABLE 1

| Mass % | Example 1 | Example 2 | Example 3 | Example 4 | Example 5 | Example 6 | Example 7 | Example 8 | Example 9 |
|---|---|---|---|---|---|---|---|---|---|
| $SiO_2$ | 60.18 | 60.69 | 61.62 | 60.37 | 62.00 | 61.14 | 61.30 | 61.46 | 60.64 |
| $Al_2O_3$ | 11.22 | 11.31 | 11.30 | 11.25 | 10.44 | 11.21 | 11.24 | 11.27 | 11.30 |
| $SiO_2$—$Al_2O_3$ | 48.96 | 49.38 | 50.32 | 49.12 | 51.57 | 49.93 | 50.05 | 50.19 | 49.34 |
| MgO | 3.26 | 3.33 | 3.21 | 3.18 | 3.08 | 2.40 | 3.07 | 3.74 | 3.30 |
| CaO | 23.37 | 23.88 | 23.08 | 22.83 | 22.10 | 22.89 | 22.03 | 21.16 | 23.71 |
| $Li_2O$ | 0.39 | 0.79 | 0.79 | 0.79 | 0.79 | 0.78 | 0.79 | 0.79 | 0.79 |
| $Na_2O$ | — | — | — | — | — | — | — | — | — |
| $K_2O$ | — | — | — | — | — | — | — | — | — |
| $Li_2O + Na_2O + K_2O$ | 0.39 | 0.79 | 0.79 | 0.79 | 0.79 | 0.78 | 0.79 | 0.79 | 0.79 |
| $TiO_2$ | 1.57 | — | — | 1.58 | 1.58 | 1.57 | 1.58 | 1.58 | 0.26 |
| $Fe_2O_3$ | — | — | — | — | — | — | — | — | — |
| Glass transition point [° C.] | 722 | 697 | 695 | 695 | 686 | 699 | 695 | 681 | 695 |
| Softening point [° C.] | 872 | 860 | 867 | 858 | 864 | 864 | 862 | 866 | 860 |
| Devitrification temp. [° C.] | 1208 | 1210 | 1207 | 1196 | 1197 | 1195 | 1189 | 1210 | 1198 |
| Working temp. [° C.] | 1216 | 1214 | 1219 | 1209 | 1216 | 1212 | 1227 | 1222 | 1205 |
| ΔT [° C.] | 8 | 4 | 12 | 13 | 19 | 17 | 38 | 12 | 7 |
| ΔK [° C.] | 344 | 354 | 352 | 351 | 352 | 348 | 365 | 356 | 345 |
| $\Delta W_1$ [mass %] | 0.26 | 0.28 | 0.21 | 0.32 | 0.21 | 0.18 | 0.18 | 0.18 | 0.28 |
| $\Delta W_2$ [mass %] | 1.55 | 1.03 | 1.05 | 1.02 | 1.47 | 1.50 | 1.50 | 1.50 | 1.03 |

TABLE 2

| Mass % | Example 10 | Example 11 | Example 12 | Example 13 | Example 14 | Example 15 | Example 16 | Example 17 | Example 18 |
|---|---|---|---|---|---|---|---|---|---|
| $SiO_2$ | 60.57 | 60.51 | 60.44 | 60.56 | 61.13 | 61.17 | 61.04 | 61.56 | 61.03 |
| $Al_2O_3$ | 11.29 | 11.28 | 11.27 | 11.29 | 11.40 | 11.22 | 11.19 | 11.29 | 11.19 |
| $SiO_2$—$Al_2O_3$ | 49.28 | 49.23 | 49.17 | 49.27 | 49.74 | 49.95 | 49.84 | 50.27 | 49.84 |
| MgO | 3.30 | 3.29 | 3.29 | 3.10 | 2.87 | 3.06 | 3.06 | 3.19 | 2.95 |
| CaO | 23.68 | 23.66 | 23.63 | 22.28 | 20.61 | 21.98 | 21.94 | 22.90 | 21.16 |
| $Li_2O$ | 0.69 | 0.69 | 0.59 | 1.19 | 2.39 | 0.59 | 0.59 | 0.79 | 0.78 |
| $Na_2O$ | 0.20 | — | 0.20 | — | — | 0.41 | — | — | — |
| $K_2O$ | — | 0.31 | 0.31 | — | — | — | 0.62 | — | — |
| $Li_2O + Na_2O + K_2O$ | 0.89 | 1.00 | 1.10 | 1.19 | 2.39 | 1.00 | 1.20 | 0.79 | 0.78 |
| $TiO_2$ | 0.26 | 0.26 | 0.26 | 1.58 | 1.60 | 1.57 | 1.57 | 0.26 | 2.88 |
| $Fe_2O_3$ | — | — | — | — | — | — | — | — | — |
| Glass transition point [° C.] | 696 | 698 | 702 | 655 | 648 | 702 | 704 | 695 | 687 |
| Softening point [° C.] | 862 | 862 | 866 | 838 | 795 | 873 | 872 | 867 | 863 |
| Devitrification temp. [° C.] | 1188 | 1191 | 1192 | 1186 | 1164 | 1198 | 1197 | 1203 | 1197 |
| Working temp. [° C.] | 1207 | 1206 | 1210 | 1190 | 1164 | 1226 | 1224 | 1219 | 1217 |
| ΔT [° C.] | 19 | 15 | 18 | 4 | 0 | 28 | 27 | 16 | 20 |
| ΔK [° C.] | 345 | 344 | 344 | 352 | 369 | 353 | 352 | 352 | 354 |
| $\Delta W_1$ [mass %] | 0.26 | 0.26 | 0.27 | 0.24 | 0.32 | 0.18 | 0.18 | 0.20 | 0.24 |
| $\Delta W_2$ [mass %] | 1.09 | 1.09 | 1.11 | 1.31 | 0.98 | 1.55 | 1.55 | 1.10 | 1.66 |

TABLE 3

| Mass % | Example 19 | Example 20 |
|---|---|---|
| $SiO_2$ | 61.51 | 60.97 |
| $Al_2O_3$ | 11.28 | 11.18 |
| $SiO_2$—$Al_2O_3$ | 50.23 | 49.79 |
| MgO | 3.20 | 3.12 |
| CaO | 22.96 | 22.37 |
| $Li_2O$ | 0.79 | 0.78 |
| $Na_2O$ | — | — |
| $K_2O$ | — | — |
| $Li_2O + Na_2O + K_2O$ | 0.79 | 0.78 |
| $TiO_2$ | — | — |
| $Fe_2O_3$ | 0.26 | 1.57 |
| Glass transition point [° C.] | 697 | 689 |
| Softening point [° C.] | 867 | 868 |
| Devitrification temp. [° C.] | 1205 | 1208 |
| Working temp. [° C.] | 1221 | 1221 |
| ΔT [° C.] | 16 | 13 |
| ΔK [° C.] | 354 | 353 |
| $\Delta W_1$ [mass %] | 0.21 | 0.21 |
| $\Delta W_2$ [mass %] | 1.05 | 1.05 |

TABLE 4

| Mass % | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| $SiO_2$ | 72.76 | 59.00 | 59.10 | 58.35 | 57.95 | 57.65 | 57.60 | 59.63 | 61.01 |
| $Al_2O_3$ | 1.88 | 12.10 | 13.10 | 13.20 | 13.20 | 13.40 | 14.41 | 11.12 | 11.37 |
| $SiO_2$—$Al_2O_3$ | 70.88 | 46.90 | 46.00 | 45.15 | 44.75 | 44.25 | 43.18 | 48.51 | 49.64 |
| MgO | 3.58 | 3.40 | 2.83 | 2.55 | 2.55 | 2.55 | 3.14 | — | 5.90 |

TABLE 4-continued

| Mass % | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| CaO | 7.62 | 22.60 | 24.31 | 23.65 | 24.05 | 24.15 | 22.52 | 26.92 | 19.33 |
| $Li_2O$ | — | — | — | 0.90 | 0.90 | 0.90 | 0.78 | 0.78 | 0.80 |
| $Na_2O$ | 13.20 | 0.90 | 0.03 | — | — | — | — | — | — |
| $K_2O$ | 0.95 | — | 0.23 | — | — | — | — | — | — |
| $Li_2O + Na_2O + K_2O$ | 14.15 | 0.90 | 0.26 | 0.90 | 0.90 | 0.90 | 0.78 | 0.78 | 0.80 |
| $TiO_2$ | — | 1.50 | 0.04 | 1.10 | 1.10 | 1.10 | 1.56 | 1.56 | 1.60 |
| $Fe_2O_3$ | — | 0.20 | 0.36 | 0.25 | 0.25 | 0.25 | — | — | — |
| Glass transition point [° C.] | 553 | 738 | 758 | 702 | 702 | 702 | 704 | 706 | 688 |
| Softening point [° C.] | 729 | 884 | 885 | 855 | 852 | 852 | 865 | 850 | 853 |
| Devitrification temp. [° C.] | 1020 | 1210 | 1202 | 1168 | 1181 | 1184 | 1203 | 1298 | 1264 |
| Working temp. [° C.] | 1172 | 1232 | 1246 | 1196 | 1191 | 1190 | 1206 | 1211 | 1216 |
| ΔT [° C.] | 152 | 22 | 44 | 28 | 10 | 6 | 3 | −87 | −48 |
| ΔK [° C.] | 443 | 348 | 361 | 341 | 339 | 338 | 341 | 361 | 363 |
| $\Delta W_1$ [mass %] | 0.40 | 1.04 | 0.90 | 1.18 | 1.34 | 1.43 | 1.64 | 0.24 | 0.24 |
| $\Delta W_2$ [mass %] | 14.20 | 1.26 | 1.27 | 1.11 | 1.03 | 1.03 | 1.18 | 1.46 | 1.46 |

TABLE 5

| Mass % | Comparative Example 10 | Comparative Example 11 | Comparative Example 12 | Comparative Example 13 | Comparative Example 14 | Comparative Example 15 | Comparative Example 16 |
|---|---|---|---|---|---|---|---|
| $SiO_2$ | 60.78 | 60.43 | 60.00 | 59.87 | 59.37 | 62.31 | 60.00 |
| $Al_2O_3$ | 11.15 | 11.08 | 11.18 | 11.16 | 11.07 | 11.62 | 11.00 |
| $SiO_2—Al_2O_3$ | 49.63 | 49.35 | 48.82 | 48.71 | 48.30 | 50.69 | 48.99 |
| MgO | 3.04 | 3.07 | 3.33 | 3.15 | 3.13 | 2.39 | 2.48 |
| CaO | 21.84 | 22.03 | 23.92 | 22.64 | 22.45 | 17.17 | 17.78 |
| $Li_2O$ | — | — | — | — | — | 4.88 | 0.77 |
| $Na_2O$ | 1.62 | — | — | 1.62 | — | — | — |
| $K_2O$ | — | 1.83 | — | — | 2.44 | — | — |
| $Li_2O + Na_2O + K_2O$ | 1.62 | 1.83 | 0.00 | 1.62 | 2.44 | 4.88 | 0.77 |
| $TiO_2$ | 1.56 | 1.56 | 1.57 | 1.57 | 1.55 | 1.63 | 7.98 |
| $Fe_2O_3$ | — | — | — | — | — | — | — |
| Glass transition point [° C.] | 738 | 741 | 754 | 727 | 745 | 578 | 675 |
| Softening point [° C.] | 892 | 883 | 882 | 891 | 881 | 701 | 864 |
| Devitrification temp. [° C.] | 1211 | 1214 | 1214 | 1214 | 1237 | 1111 | 1278 |
| Working temp. [° C.] | 1246 | 1257 | 1246 | 1239 | 1253 | 1097 | 1211 |
| ΔT [° C.] | 35 | 43 | 32 | 25 | 16 | −14 | −67 |
| ΔK [° C.] | 354 | 374 | 364 | 348 | 372 | 396 | 347 |
| $\Delta W_1$ [mass %] | 0.24 | 0.24 | 0.33 | 0.33 | 0.33 | 0.36 | 0.47 |
| $\Delta W_2$ [mass %] | 1.61 | 1.61 | 1.59 | 1.59 | 1.59 | 0.95 | 1.67 |

The glass transition points of the glasses according to Examples 1 to 20 were 648° C. to 722° C. This indicates that these glasses have excellent heat resistance.

The working temperatures of these glasses were 1164° C. to 1227° C. These temperatures are suitable for producing glass flakes.

The differences ΔT (working temperature—devitrification temperature) of these glasses were 0° C. to 38° C. These differences do not cause devitrification in the process of producing glass flakes.

The differences ΔK (working temperature—softening point temperature) of these glasses were 344° C. to 369° C. These temperature differences are suitable for adjusting the thickness of the glass flakes.

Furthermore, these glasses had mass reduction rates $\Delta W_1$, the index of acid resistance, of 0.18 mass % to 0.32 mass %. This indicates that these glass flakes have excellent acid resistance.

Moreover, these glasses had mass reduction rates $\Delta W_2$, the index of alkali resistance, of 0.98 mass % to 1.66 mass %. This indicates that these glass flakes have excellent alkali resistance.

The glass of Comparative Example 1 was made of a sheet glass composition (soda-lime composition) that had been provided conventionally. However, this glass had a glass transition point of lower than 600° C. Thus it was proved that the heat resistance thereof was not sufficiently high. Furthermore, the glass had a mass reduction rate $\Delta W_2$ of 14.20 mass %, which was higher than the mass reduction rates $\Delta W_2$ of the glasses according to Examples 1 to 20.

The glass of Comparative Example 2 had the glass composition described in an example of JP 61(1986)-14152 A. The working temperature of the glass was 1232° C., which was higher than the working temperatures of the glasses according to Examples 1 to 20. Furthermore, the mass reduction rate $\Delta W_1$ of the glass was 1.04 mass %, which was higher than the mass reduction rates $\Delta W_1$ of the glasses according to Examples 1 to 20.

The glass of Comparative Example 3 had the composition described in Example V of JP 2001-515448 A. The working temperature of the glass was 1246° C., which was higher than the working temperatures of the glasses according to Examples 1 to 20. Furthermore, the mass reduction rate $\Delta W_1$ of the glass was 0.90 mass %, which was higher than the mass reduction rates $\Delta W_1$ of the glasses according to Examples 1 to 20.

The glass of Comparative Example 4 had the glass composition described in Example 85 of JP 2003-500330 A. The difference ΔK (working temperature—softening point temperature) of the glass was 341° C., which was smaller than the differences ΔK of the glasses according to Examples 1 to 20. Furthermore, the mass reduction rate $\Delta W_1$ of the glass was 1.18 mass %, which was higher than the mass reduction rates $\Delta W_1$ of the glasses according to Examples 1 to 20.

The glass of Comparative Example 5 had the glass composition described in Example 90 of JP 2004-508265 A. The difference ΔK (working temperature—softening point temperature) of the glass was 339° C., which was smaller than the differences ΔK of the glasses according to Examples 1 to 20. Furthermore, the mass reduction rate $\Delta W_1$ of the glass was 1.34 mass %, which was higher than the mass reduction rates $\Delta W_1$ of the glasses according to Examples 1 to 20.

The glass of Comparative Example 6 had the glass composition described in Example 124 of JP 2005-506267 A. The difference ΔK (working temperature—softening point temperature) of the glass was 338° C., which was smaller than the differences ΔK of the glasses according to Examples 1 to 20. Furthermore, the mass reduction rate $\Delta W_1$ of the glass was 1.43 mass %, which was higher than the mass reduction rates $\Delta W_1$ of the glasses according to Examples 1 to 20.

The difference ΔK (working temperature—softening point temperature) of the glass of Comparative Example 7 was 341° C., which was smaller than the differences ΔK of the glasses according to Examples 1 to 20. Furthermore, the mass reduction rate $\Delta W_1$ of the glass was 1.64 mass %, which was higher than the mass reduction rates $\Delta W_1$ of the glasses according to Examples 1 to 20.

The difference ΔT (working temperature—devitrification temperature) of the glass of Comparative Example 8 was −87° C., which was smaller than the differences ΔT of the glasses according to Examples 1 to 20.

The difference ΔT (working temperature—devitrification temperature) of the glass of Comparative Example 9 was −48° C., which was smaller than the differences ΔT of the glasses according to Examples 1 to 20.

The working temperature of the glass of Comparative Example 10 was 1246° C., which was higher than the working temperatures of the glasses according to Examples 1 to 20.

The working temperature of the glass of Comparative Example 11 was 1257° C., which was higher than the working temperatures of the glasses according to Examples 1 to 20.

The working temperature of the glass of Comparative Example 12 was 1246° C., which was higher than the working temperatures of the glasses according to Examples 1 to 20.

The working temperature of the glass of Comparative Example 13 was 1239° C., which was higher than the working temperatures of the glasses according to Examples 1 to 20.

The working temperature of the glass of Comparative Example 14 was 1253° C., which was higher than the working temperatures of the glasses according to Examples 1 to 20.

The difference ΔT (working temperature—devitrification temperature) of the glass of Comparative Example 15 was −14° C., which was smaller than the differences ΔT of the glasses according to Examples 1 to 20. Moreover, this glass had a glass transition point of lower than 600° C. Thus it was proved that the heat resistance thereof was not sufficiently high.

The difference ΔT (working temperature—devitrification temperature) of the glass of Comparative Example 16 was −67° C., which was larger than the differences ΔT of the glasses according to Examples 1 to 20.

The glass of Example 4 had a composition obtained by adjusting the contents of $SiO_2$ and $Al_2O_3$ used in Comparative Example 7. The increased content of ($SiO_2$—$Al_2O_3$) enlarged the difference ΔK and reduced the mass reduction rate $\Delta W_1$.

The glasses of Examples 4, 13, and 14 respectively had a composition obtained by adjusting the content of $Li_2O$ used in Example 1. The working temperatures of these glasses were 1164° C. to 1209° C. The differences ΔK (working temperature—softening point temperature) were 351° C. to 369° C. The increased contents of $Li_2O$ lowered the working temperatures and enlarged the differences ΔK.

It has been found that the acid resistance, working temperature, and temperature difference ΔK obtained by subtracting the softening point temperature from the working temperature varies according to the values of ($SiO_2$—$Al_2O_3$) and $Li_2O$ in the composition of the glass according to the present invention. Furthermore, it has been proved that the glasses in which the contents of $SiO_2$ and $Al_2O_3$ as well as the value of ($SiO_2$—$Al_2O_3$) are within the composition range of the present invention have excellent acid resistance and formability. Therefore it has been proved that the value of ($SiO_2$—$Al_2O_3$) is effective as an index of the acid resistance and formability of glasses.

Glasses having the compositions of the present invention were found to have excellent alkali resistance.

Subsequently, with glasses of Examples 1 to 20, glass flakes and glass flakes with a coating film were produced. First, glass having each composition was remelted in an electric furnace. This was formed into pellets while being cooled. These pellets were placed in a production apparatus as shown in FIG. 1 and thus glass flakes with an average thickness of 0.5 to 1 μm were produced.

Application Examples 1 to 6

Glass flakes thus produced having the compositions of Examples 2, 4, 7, 9, 14 and 17 each were crushed to have suitable grain sizes. Thereafter, the surfaces of the glass flakes were coated with titanium oxide by a liquid phase method. This liquid phase method was one described in JP 2003-12962A, i.e. a method of allowing titanium dioxide to deposit on the surfaces of glass flakes from metal salt. The glass flakes with a coating film thus produced were observed with an electron microscope and thereby it was confirmed that a titanium dioxide coating film had been formed on the surface of each glass flake.

Application Examples 7 to 12

Glass flakes having the compositions of Examples 2, 4, 7, 9, 14 and 17 each were crushed to have suitable grain sizes. Thereafter, the surfaces of the glass flakes were coated with silver by common electroless plating. This common electroless plating was one described in Comparative Example 2 of JP 2003-12962 A. The glass flakes with a coating film thus produced were observed with an electron microscope and thereby it was confirmed that a silver coating film had been formed on the surface of each glass flake.

Application Examples 13 to 18

Glass flakes having the compositions of Examples 2, 4, 7, 9, 14, and 17 each were crushed to have suitable grain sizes. Thereafter, this was mixed with polyester resin and thereby a polyester resin composition containing glass flakes was obtained.

Application Examples 19 to 24

The glass flakes with a coating film of Application Examples 1 to 6 each were mixed with epoxy acrylate and thereby a vinyl ester coating material containing glass flakes with a coating film was obtained.

Application Examples 25 to 30

The glass flakes with a coating film of Application Examples 1 to 6 each were mixed with foundation, a facial cosmetic, and thereby a cosmetic containing glass flakes with a coating film was obtained.

Application Examples 31 to 36

The glass flakes with a coating film of Application Examples 1 to 6 each were mixed with an ink composition obtained by suitably mixing a colorant, resin, and an organic solvent, and thereby an ink composition containing glass flakes with a coating film was obtained.

The invention claimed is:

1. A glass flake, having a composition comprising, in terms of mass %:

$60 < SiO_2 \leq 65$, $8 \leq Al_2O_3 < 12$, $49 \leq (SiO_2—Al_2O_3) \leq 57$, $1 \leq MgO \leq 5$, $18 \leq CaO \leq 30$, $2 < Li_2O \leq 4$ $2 < (Li_2O + Na_2O + K_2O) \leq 4$, $0 \leq TiO_2 \leq 5$, and the composition containing each of $B_2O_3$, F, ZnO, BaO, SrO, and $ZrO_2$ in amounts lower than 0.1 mass %, and wherein the glass flake has an index of acid resistance in terms of a mass reduction rate $\Delta W_1$ of 0.80 mass % or lower.

2. The glass flake according to claim 1, wherein when a temperature at which glass has a viscosity of 1000 dPa·sec is defined as a working temperature, the working temperature is 1230° C. or lower.

3. The glass flake according to claim 2, wherein a temperature difference $\Delta T$ obtained by subtracting a devitrification temperature from the working temperature of the glass is at least 0° C.

4. The glass flake according to claim 2, wherein a temperature difference $\Delta K$ obtained by subtracting a softening point temperature from the working temperature of the glass is at least 342° C.

5. A glass flake with a coating film, comprising:
the glass flake according to claim 1; and
a coating film that is composed mainly of metal and/or metal oxide and that covers a surface of the glass flake.

6. The glass flake with a coating film according to claim 5, wherein the metal is at least one selected from the group consisting of nickel, gold, silver, platinum, and palladium.

7. The glass flake with a coating film according to claim 5, wherein the metal oxide is at least one selected from the group consisting of titanium oxide, aluminum oxide, iron oxide, cobalt oxide, zirconium oxide, zinc oxide, tin oxide, and silicon oxide.

8. A resin composition comprising the glass flake according to claim 1 or the glass flake of with a coating film that is composed mainly of metal and/or metal oxide and that covers a surface of the glass flake.

9. A coating material comprising the glass flake according to claim 1 or the glass flake of with a coating film that is composed mainly of metal and/or metal oxide and that covers a surface of the glass flake.

10. An ink composition comprising the glass flake according to claim 1 or the glass flake of with a coating film that is composed mainly of metal and/or metal oxide and that covers a surface of the glass flake.

11. A cosmetic comprising the glass flake according to claim 1 or the glass flake of with a coating film that is composed mainly of metal and/or metal oxide and that covers a surface of the glass flake.

12. The glass flake according to claim 1, wherein the mass reduction rate $\Delta W_1$ is 0.50 mass % or lower.

13. The glass flake according to claim 1, wherein the glass flake has an index of alkali resistance in terms of a mass reduction rate $\Delta W_2$ of 3 mass % or lower.

14. A glass flake, having a composition comprising, in terms of mass %:

$61.04 \leq SiO_2 \leq 65$, $8 \leq Al_2O_3 < 12$, $49.84 \leq (SiO_2—Al_2O_3) \leq 57$, $3.06 \leq MgO \leq 3.74$, $18 \leq CaO \leq 21.98$, $0.4 \leq Li_2O \leq 4$ $0 < (Li_2O + Na_2O + K_2O) \leq 4$, $1.57 \leq TiO_2 \leq 5$, and the composition containing each of $B_2O_3$, F, ZnO, BaO, SrO, and $ZrO_2$ lower than 0.1 mass %, wherein a content ratio of $SiO_2$ to (MgO+CaO) is no less than 2.37 and no greater than 3.09, and wherein the glass flake has an index of acid resistance in terms of a mass reduction rate $\Delta W_1$ of 0.80 mass % or lower.

15. The glass flake according to claim 14, wherein when a temperature at which glass has a viscosity of 1000 dPa·sec is defined as a working temperature, the working temperature is 1230° C. or lower.

16. The glass flake according to claim 15, wherein a temperature difference $\Delta T$ obtained by subtracting a devitrification temperature from the working temperature of the glass is at least 0° C.

17. The glass flake according to claim 15, wherein a temperature difference $\Delta K$ obtained by subtracting a softening point temperature from the working temperature of the glass is at least 342° C.

18. A glass flake with a coating film, comprising:
the glass flake according to claim 14; and
a coating film that is composed mainly of metal and/or metal oxide and that covers a surface of the glass flake.

19. The glass flake with a coating film according to claim 18, wherein the metal is at least one selected from the group consisting of nickel, gold, silver, platinum, and palladium.

20. The glass flake with a coating film according to claim 18, wherein the metal oxide is at least one selected from the group consisting of titanium oxide, aluminum oxide, iron oxide, cobalt oxide, zirconium oxide, zinc oxide, tin oxide, and silicon oxide.

21. A resin composition comprising the glass flake according to claim 14 or the glass flake of with a coating film that is composed mainly of metal and/or metal oxide and that covers a surface of the glass flake.

22. A coating material comprising the glass flake according to claim 14 or the glass flake of with a coating film that is composed mainly of metal and/or metal oxide and that covers a surface of the glass flake.

23. An ink composition comprising the glass flake according to claim 14 or the glass flake of with a coating film that is composed mainly of metal and/or metal oxide and that covers a surface of the glass flake.

24. A cosmetic comprising the glass flake according to claim 14 or the glass flake of with a coating film that is composed mainly of metal and/or metal oxide and that covers a surface of the glass flake.

25. The glass flake according to claim 14, wherein the mass reduction rate $\Delta W_1$ is 0.50 mass % or lower.

26. The glass flake according to claim 14, wherein the glass flake has an index of alkali resistance in terms of a mass reduction rate $\Delta W_2$ of 3 mass % or lower.

27. The glass flake according to claim 14, wherein the glass flake has a $\Delta T$ of no greater than 50° C., where $\Delta T$ is obtained by subtracting a devitrification temperature from a working temperature of the glass flake.

* * * * *

UNITED STATES PATENT AND TRADEMARK OFFICE
CERTIFICATE OF CORRECTION

| | | |
|---|---|---|
| PATENT NO. | : 8,383,532 B2 | Page 1 of 1 |
| APPLICATION NO. | : 12/305850 | |
| DATED | : February 26, 2013 | |
| INVENTOR(S) | : Fujiwara et al. | |

It is certified that error appears in the above-identified patent and that said Letters Patent is hereby corrected as shown below:

In the Specification

Column 3, line 23, after "0<$Li_2O$≤4" insert -- , --.

Column 5, line 59, delete "$LiO_2$" and insert -- $Li_2O$ --.

Column 18, line 23, delete "remelted" and insert -- re-melted --.

In the Claims

Column 19, line 33, in Claim 1, after "2<$Li_2O$≤4" insert -- , --.

Column 20, line 2, in Claim 8, after "flake" delete "of".

Column 20, line 6, in Claim 9, after "flake" delete "of".

Column 20, line 10, in Claim 10, after "flake" delete "of".

Column 20, line 14, in Claim 11, after "flake" delete "of".

Column 20, line 35, in Claim 14, after "0.4≤$Li_2O$≤4" insert -- , --.

Column 21, line 5, in Claim 21, after "flake" delete "of".

Column 21, line 9, in Claim 22, after "flake" delete "of".

Column 21, line 13, in Claim 23, after "flake" delete "of".

Column 22, line 2, in Claim 24, after "flake" delete "of".

Signed and Sealed this
Eighth Day of July, 2014

Michelle K. Lee
*Deputy Director of the United States Patent and Trademark Office*